United States Patent
Olsen

(10) Patent No.: US 6,589,222 B1
(45) Date of Patent: Jul. 8, 2003

(54) OSTOMY APPLIANCE

(75) Inventor: Eskil Hoejland Olsen, Humlebaek (DK)

(73) Assignee: Coloplast A/S, Humlebaek (DK)

(*) Notice: Subject to any disclaimer, the term of this patent is extended or adjusted under 35 U.S.C. 154(b) by 0 days.

(21) Appl. No.: 09/926,053

(22) PCT Filed: Feb. 25, 2000

(86) PCT No.: PCT/DK00/00081
§ 371 (c)(1),
(2), (4) Date: Aug. 22, 2001

(87) PCT Pub. No.: WO00/49981
PCT Pub. Date: Aug. 31, 2000

(30) Foreign Application Priority Data

Feb. 25, 1999 (DK) .......................... 1999 00254

(51) Int. Cl.⁷ .................................................. A61F 5/44
(52) U.S. Cl. ........................................ 604/336; 604/337
(58) Field of Search ................................ 604/332–345

(56) References Cited

U.S. PATENT DOCUMENTS

| | | | | |
|---|---|---|---|---|
| 3,419,006 A | 12/1968 | King | .......................... | 128/268 |
| 3,972,328 A | 8/1976 | Chen | .......................... | 128/156 |
| 4,367,732 A | 1/1983 | Poulsen et al. | ............. | 128/156 |
| 4,538,603 A | 9/1985 | Pawelchak et al. | ......... | 128/156 |
| 4,552,138 A | 11/1985 | Hofeditz et al. | ............. | 128/156 |
| 4,846,820 A | 7/1989 | Jensen | ........................ | 604/339 |
| 4,867,748 A | 9/1989 | Samuelsen | .................. | 604/336 |
| 5,051,259 A | 9/1991 | Olsen et al. | .................. | 424/443 |
| 5,618,276 A | 4/1997 | Leise, Jr. et al. | ........... | 604/336 |
| 5,714,225 A | 2/1998 | Hansen et al. | ............... | 428/114 |
| 5,730,735 A | 3/1998 | Holmberg et al. | .......... | 604/338 |

FOREIGN PATENT DOCUMENTS

| | | |
|---|---|---|
| EP | 0 097 846 | 1/1984 |
| EP | 0 272 149 | 6/1988 |
| EP | 0 317 326 | 5/1989 |
| EP | 0 416 397 | 3/1991 |
| EP | 0 686 381 | 12/1995 |
| EP | 0 894 482 | 2/1999 |
| GB | 1 280 631 | 7/1972 |
| GB | 1 586 182 | 3/1981 |
| GB | 2 290 974 | 1/1996 |
| WO | 88/06894 | 9/1988 |
| WO | 95/24169 | 9/1995 |
| WO | 98/17212 | 4/1998 |
| WO | 98/53771 | 12/1998 |
| WO | 98/55057 | 12/1998 |

*Primary Examiner*—Weilun Lo
*Assistant Examiner*—Linh Truong
(74) *Attorney, Agent, or Firm*—Jacobson Holman PLLC

(57) ABSTRACT

An ostomy appliance comprising a body side member, an optionally separately exchangeable receiving member or bag secured to the body side member, said body side member comprising a ring-shaped body having an adhesive wafer having a hole for accommodating a stoma and further a separate sealing member which, when in use, is placed in the hole for sealing against the stoma, wherein the separate sealing member has a hole for accommodating the stoma and comprises a mouldable mass of a hypo-allergenic, substantially non-memory putty-like adhesive in the form of a disc, wherein the disc has an outer diameter smaller than the diameter of the hole of the wafer or pad of the ostomy body side member, wherein the disc has a flange member that is supplied with a folding zone that offers a flexible and secure means for sealing between the stoma and the body side member and may be exchanged separately leaving the body side member.

5 Claims, 2 Drawing Sheets

OSTOMY APPLIANCE

BACKGROUND OF THE INVENTION

1. Field of the Invention

The present invention relates to an ostomy appliance, an ostomy sealing member and to methods for placing an ostomy appliance on the abdomen of an ostomate.

In connection with surgery for a number of diseases in the gastro-intestinal tract a consequence is, in many cases, that the colon, the ileum or the urethra has been exposed surgically and the patient is left with an abdominal stoma and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma. Also in connection with a fistula, the patient will have to rely on an appliance to collect the bodily material emerging from such opening.

Ostomy appliances are well known. Such appliances may be two-piece or one-piece appliances. In both types of appliances, a body side member is attached to the wearer's abdomen, and, in case of a two-piece appliance, a receiving member or bag is releasably attached to the body side ostomy member for receiving exudates from the stoma.

When using one-piece appliances, the whole appliance, including the adhesive wafer or pad securing the appliance to the skin is removed and replaced by a fresh appliance. When using two-piece appliances, the body side ostomy member is left in place for several days, and only the receiving member or bag is replaced.

The production of ostomy products with a flat proximal adhesive side includes producing a plane disc of adhesive suitable for use on the human skin which is typically provided with a carrier sheet on one side (the distal) and a release liner on the other. The carrier sheet on the distal side of the adhesive is attached, e.g. by gluing or welding, to a collection bag or to a coupling part, to which a collection bag may be detachably coupled. The release liner on the proximal side of the adhesive is a protective sheet, which is removed prior to use, and the ostomy appliance is then adhered to the user's skin by means of the substantially plane proximal side of the adhesive.

The service time of the body side ostomy member depends on the amount and aggressiveness of the exudates and of the tightness of the sealing between the stoma and the body side ostomy member.

In the known appliances it is necessary to change the body side member of a two-piece appliance when the centre part of the adhesive wafer or pad has been sufficiently deteriorated to allow access of the aggressive exudates to the skin surrounding the stoma, irrespective of the fact that the wafer as such has a much longer wearing time. The access of aggressive exudates to the skin is causing skin problems.

At the same time, it is often difficult to obtain a reliable sealing between the adhesive wafer and the stoma in order to prevent the aggressive exudates from contacting the skin.

2. Description of the Related Art

Methods of overcoming the sealing problems have been proposed.

GB Patent Application No. GB 2 290 974 discloses a body-side ostomy member comprising a ring to which a bag-side coupling ring or a bag can be attached, said ring comprising a rib and a flange, said flange being mounted on a wafer of medical grade adhesive having a central whole of diameter at least 65% of the internal diameter of the ring. When applying such body-side ostomy member, a mouldable mass of non-hypoallergenic, non-memory putty-like adhesive, particularly based on hydrocolloid or hydrogel, is disposed radially inward of the wafer so that it forms a protective mass surrounding the stoma. The mouldable mass has a thickness of 1.25–3 times that of the wafer and a central hole therein of a diameter no more than 1/10 th of the internal diameter of the ring. Both the medical grade adhesive and the mouldable adhesive are adhered to the skin.

European Patent application No. EP 0 686 381 discloses an ostomy appliance comprising a collection pouch and faceplate assembly including a flexible patch having a stoma-receiving opening, a first layer of skin-friendly hydrocolloid-containing adhesive material along one side of said patch about said opening for securing said faceplate assembly to peristomal skin surfaces, and a second layer of relatively soft, easily deformable and extrudable, adhesive sealant material of a composition that is resistant to being dissolved or disintegrated by stomal fluids and that immediately surrounds said opening; said second layer being displaceable inwardly and axially into said opening for forming a stoma-engaging annular gasket to prevent stomal fluids from contacting the peristomal skin and said first adhesive layer.

These references, however, do not address the problem that the appliance as a whole must be replaced and thus, the remaining life-time of the part of the adhesive wafer securing the appliance to the abdomen of the ostomate is not utilised and the skin is exposed to an undesirable stress due to many exchanges of the appliance.

In ostomy patients it is frequently seen that the immediate surroundings of the stoma, at a distance of 1–2 cm, are recessed or are positioned in a crater or a cavity as compared to the rest of the skin surface surrounding the stoma. For such patients it has been found to be expedient to use an ostomy product where the adhesive surface around the opening for receiving the stoma has a part which is convex and protrudes toward the user in order to enable the adhesive face of the ostomy appliance to contact and adhere to essentially the entire surface of the skin in the crater or the cavity. In particular, it is important that the ostomy appliance adheres well to the skin in the area next to the stoma in order to give security against deterioration of the adhesive and against leakage. The use of an adhesive wafer having a rigid convex shape may also apply an external pressure to the area next to the stoma which, in particularly in connection with recessed stomas, will ensure a sufficient protrusion of the stoma to aid the discharge of effluents therefrom directly into the collection bag without contacting the exposed adhesive next to the stoma and prolong the time of service of the adhesive wafer or plate. The shape of the protruding part of the adhesive face may e.g. be domed or conical, and such products are known under the designation convex products.

EP 317 326 describes a convex product having a rigid ring carrying on its entire convex side an intermediate ring of a soft thermoplastic foam material adhered to the rigid ring.

European Patent Application and EP 416 397 describes convex products where a layer of adhesive suitable for use on the human skin is arranged directly on the convex face of a ring-shaped body.

U.S. Pat. No. 5,618,276 discloses an ostomy appliance in which a thermoplastic convex pressure ring also functions as a belt attachment ring. The pressure ring is directly and sealingly secured on its convex side to an adhesive faceplate and it is also directly and sealingly secured on its opposite side to a collection pouch.

WO 95/24169 discloses an ostomy appliance comprising a ring-shaped body having a convex proximal side and a distal side as well as an inner periphery and an outer periphery, a layer of adhesive to attach the ring-shaped body to a user's skin with the proximal side facing the user's skin, which adhesive is present on a thermoplastic carrier sheet having at least the same extent as the adhesive, and wherein the carrier sheet is disposed between the adhesive and the ring-shaped body and is attached to the proximal side of the ring-shaped body along the inner periphery and the outer periphery thereof with mutual spaces.

EP 0 894 482 discloses an ostomy appliance comprising a ring-shaped body having a convex proximal side and a distal side as well as an inner periphery and an outer periphery, a layer of adhesive to attach the ring-shaped body to a user's skin with the proximal side facing the user's skin, said adhesive being present on a thermoplastic carrier sheet having at least the same extent as the adhesive, disposed between the adhesive and the ring-shaped body wherein the carrier sheet is attached to the proximal side of the ring-shaped body along the outer periphery thereof and optionally along the inner periphery and wherein a further adhesive layer is present in the area between the inner and outer periphery.

None of these references address the problem of providing a seal between the adhesive plate of the appliance and the ostomy for preventing skin problems due to contact between the bodily material emerging from the stoma and the skin surrounding the same.

WO 98/17212 discloses an ostomy appliance comprising a body side member comprising an adhesive wafer or pad for securing the appliance to the user's skin, said wafer or pad having a hole for receiving a stoma, and an optionally separately exchangeable receiving member or bag secured to the body side ostomy member for receiving secretions from the stoma said ostomy appliance further comprising a separate sealing member disposed in the hole of the wafer or pad surrounding the stoma.

Furthermore, there is often a problem in that, due to a retracted stoma in which case is often used a convex product or in case of skin problems or folds or other irregularities, it may be difficult to place the body side member centrally with respect to the stoma. The result is that the stoma is often situated shifted with respect to the centre of the hole in the adhesive wafer for accommodating the stoma. In such cases it is especially difficult to obtain a reliable sealing between the adhesive plate of the appliance and the ostomy. No solution to this problem is offered or indicated in the above references.

It has been found that all the above problems may be overcome using the solution provided with the present invention.

SUMMARY OF THE INVENTION

The invention relates to an ostomy appliance comprising a body side member, an optionally separately exchangeable receiving member or bag secured to the body side member, said body side member comprising a ring-shaped body having an adhesive wafer having a hole for accommodating a stoma and further a separate sealing member which, when in use, is placed in the hole for sealing against the stoma, wherein the separate sealing member has a hole for accommodating the stoma and comprises a mouldable mass of a hypo-allergenic, substantially non-memory putty-like adhesive is in the form of a disc, wherein the disc has an outer diameter smaller than the diameter of the hole of the wafer or pad of the ostomy body side member, wherein the disc has a flange member stretching from its outer rim, and wherein the flange has outer dimensions greater than the diameter of the hole of the body side member for coupling to the body side member.

Furthermore, the invention relates to an ostomy sealing member in the form of a mouldable mass of a hypo-allergenic, substantially non-memory putty-like adhesive in the form of a disc, said disc having a hole for accommodating a stoma, and said disc having a flange member stretching from its outer rim.

Still further, the invention relates to methods for placing an ostomy appliance on the abdomen of an ostomate around a stoma or fistula for collecting bodily material emerging from such opening, in which an ostomy appliance comprising a body side member, an optionally separately exchangeable receiving member or bag secured to the body side member, said body side member comprising a ring-shaped body having an adhesive wafer having a hole for accommodating the stoma and further a separate sealing member which, in use, is placed in the hole for sealing against the stoma.

BRIEF DESCRIPTION OF THE DRAWINGS

The invention is disclosed more in detail with reference to the drawings in which.

DETAILED DESCRIPTION OF THE PRESENT INVENTION

Figure 1:
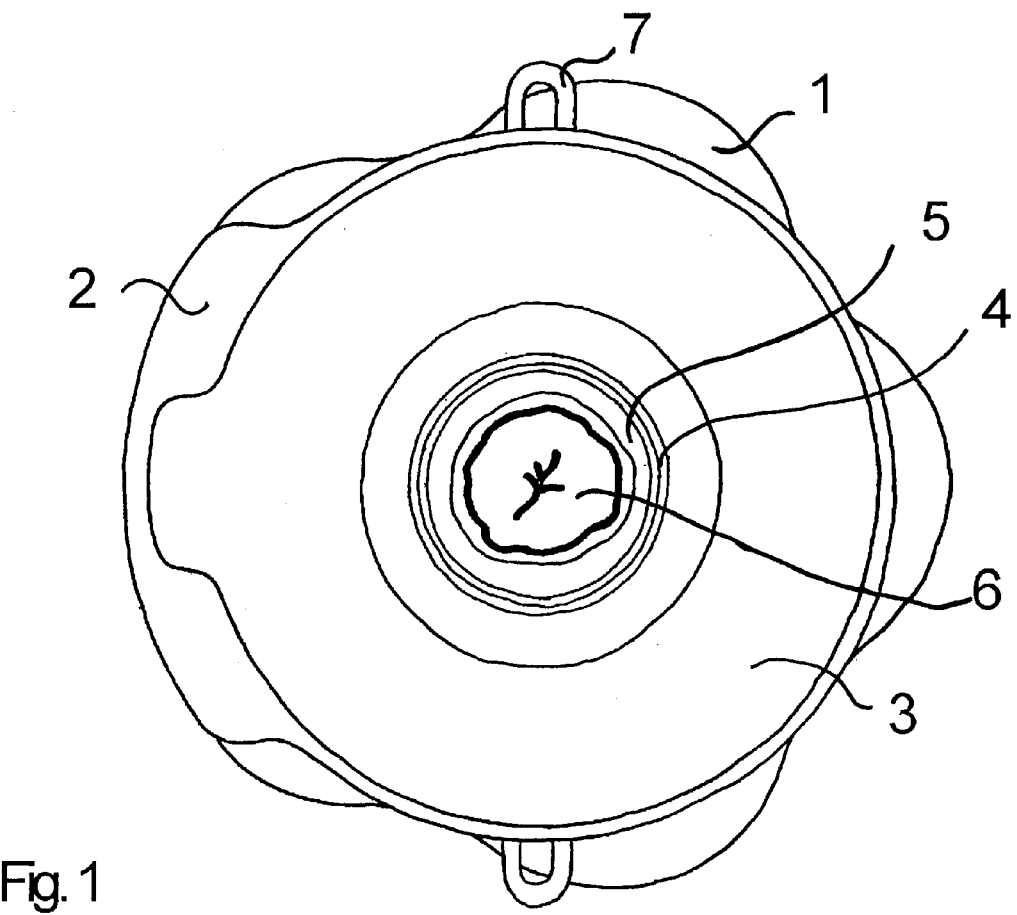
FIG. 1 shows an embodiment of an ostomy appliance according to the invention seen from the distal side.

In a first aspect, the invention relates to an ostomy appliance comprising a body side member, an optionally separately exchangeable receiving member or bag secured to the body side member, said body side member comprising a ring-shaped body having an adhesive wafer having a hole for accommodating a stoma and further a separate sealing member which, when in use, is placed in the hole for sealing against the stoma, wherein the separate sealing member has a hole for accommodating the stoma and includes a mouldable sealing body of a hypo-allergenic, substantially non-memory putty-like adhesive in the form of a disc, wherein the disc has an outer diameter smaller than the diameter of the hole of the wafer or pad of the ostomy body side member, and a flange member stretching from an outer rim of the disc, and wherein the flange has outer dimensions greater than the diameter of the hole of the body side member for coupling to the body side member and the flange member is supplied with a folding zone.

The folding zone is preferably in the form of a corrugated zone providing an extra flexibility of the flange which allows an eccentric displacement of the sealing body as compared to the flange. The corrugation may be any suitable corrugation having more smooth or more sharp corrugations. If the flange is sufficiently thin, flexibility may not require further profiling. However, it may be desirable and preferred to provide the folding zone with corrugations in more than one direction in order to enable an easy displacement sideways.

Furthermore, the folding zone renders it convenient to utilise a separate sealing member in combination with body side members having a ringshaped body having a convex proximal surface which is considered a preferred embodiment of the invention.

The ostomy appliance according to the invention offers a very high degree of freedom when placing the adhesive wafer for securing the appliance on the skin of the ostomate and allows a wider range of choice in finding at the most suitable site for placing the wafer considering the topography and skin conditions whereafter a separate sealing member may easily be placed on the body side member and the hole for accommodating the stoma is simply aligned with the stoma and the sealing member may be moulded snugly around the stoma.

It is preferred that the outer diameter of the sealing member is smaller than the inner diameter of the hole in the adhesive wafer of the appliance for allowing a different centring of the sealing member and the ostomy appliance. The difference in diameters is suitably above 1 mm and more preferred above 3 mm providing a sufficiently great degree of freedom for placing the appliance.

The flange of the sealing member of the invention preferably provides a sealing contact to the distal surface of the body-side member. Thus, a perfect filling of the gap between the sealing member and the rim of the hole of the body side member is not critical and the sealing member only needs to be moulded snugly around the stoma for excluding contact of the material emerging form the stoma and the skin surrounding the stoma or the adhesive wafer.

In an ostomy appliance according to the invention comprising a separate body side member said body side member comprises attachment means for attaching an ostomy collection bag to the body side member. Such attachment means may be a system known per se comprising matching coupling rings or matching flanges and adhesive surfaces.

In a preferred embodiment the attachment means for attaching an ostomy collection bag is matching flanges and adhesive surfaces.

In a second aspect the invention relates to an ostomy sealing member in the form of a mouldable mass of a hypo-allergenic, substantially non-memory putty-like adhesive in the form of a disc, said disc having a hole for accommodating a stoma, said disc having a flange member stretching from its outer rim, and said flange member being supplied with a folding zone.

The sealing member of the invention offers a simple and reliable solution on the above problems as the sealing around the stoma and the sealing between a separate sealing member and sealing to the body side member may be established separately and also enables a relatively unproblematic sealing, even in cases wherein there is a considerable difference in level between the area around the stoma and the surface of the body side member to which the sealing member is to be attached.

The flange member is preferably provided with an adhesive surface for securing the flange and the sealing member to the body side member. The sealing member of the invention may be used together with an ostomy body side member known per se. In such case it is preferred to choose a body side member having a hole as large as possible and to choose a sealing member having a suitably minor diameter as indicated above. The sealing member of the invention is especially preferred in connection with use of convex ostomy appliances in which cases the area around the stoma may be narrow and the difference in level between the surface of the skin and the distal surface of the body side member may be considerable.

In a third aspect, the invention relates to a method for placing an ostomy appliance on the abdomen of an ostomate around a stoma or fistula for collecting bodily material emerging from such opening, in which an ostomy appliance comprises a body side member, an optionally separately exchangeable receiving member or bag secured to the body side member, said body side member comprising a ring-shaped body having an adhesive wafer having a hole for accommodating a stoma and further a separate sealing member which, when in use, is placed in the hole for sealing against the stoma, wherein the separate sealing member has a hole for accommodating the stoma and comprises a mouldable mass of a hypo-allergenic, substantially non-memory putty-like adhesive in the form of a disc, wherein the disc has an outer diameter smaller than the diameter of the hole of the wafer or pad of the ostomy body side member, wherein the disc has having a flange member stretching from its outer rim, said flange having outer dimensions greater than the diameter of the hole of the body side member for coupling to the body side member, and wherein the flange member is supplied with a folding zone, said method comprising placing the body side member in a manner in which the stoma is essentially centrally located in the hole and in which the adhesive wafer is ensured optimum grip, whereafter the separate sealing member is shifted in such a manner that the hole therein is aligned with the stoma and the sealing member is brought into contact with the skin and moulded so as to obtain a sealing contact with the stoma.

In a fourth aspect the invention relates to a slightly modified method for placing an ostomy appliance on the abdomen of an ostomate around a stoma or fistula for collecting bodily material emerging from such opening, said ostomy appliance comprising a body side member, an optionally separately exchangeable receiving member or bag secured to the body side member, said body side member comprising a ring-shaped body having an adhesive wafer having a hole for accommodating the stoma and further a separate sealing member which, when in use, is placed in the hole for sealing against the stoma, wherein the separate sealing member has a hole for accommodating the stoma and comprises a mouldable mass of a hypo-allergenic, substantially non-memory putty-like adhesive in the form of a disc, wherein the disc has an outer diameter smaller than the diameter of the hole of the wafer or pad of the ostomy body side member, wherein the disc has a flange member stretching from its outer rim, said flange having outer dimensions greater than the diameter of the hole of the body side member for coupling to the body side member and said flange member being supplied with a folding zone, said method comprising placing the separate sealing member in such a manner that the hole therein is aligned with the stoma and the sealing member is brought into contact with the skin whereafter the body side member is shifted in such a manner that the hole therein is surrounding the stoma and the sealing member and the body side member is brought into contact with the skin, whereafter the sealing member is moulded so as to contact the stoma.

This method is possible to carry out when the sealing member may be pressed through the hole of the ostomy appliance during the application of the appliance due to flexibility of the flange. Thus, handling of two separate units may be avoided and it is also possible to obtain an easier application of one-piece appliances having a sealing member of the invention placed inside the appliance.

The adhesive wafer of an ostomy appliance may be made from any appropriate skin friendly material known per se for the purpose and may also comprise a top film known per se. The skin-friendly adhesive may be any skin-friendly adhesive known per se, e.g. an adhesive comprising hydrocolloids or other moisture absorbing constituents for prolonging the time of use. The adhesive may suitably be of the type disclosed in those disclosed in GB Patent Specifications Nos. 1 280 631, and 1 586 182, in EP Published Applications Nos. 0 097 846, 0 272 149 and 0 415 183, in WO Publication No. 88/06894, and in U.S. Pat. Nos. 3,419,006, 3,972,328, 4,538,603, and 4,867,748. Especially preferred are the adhesives disclosed in U.S. Pat. Nos. 4,367,732, 5,051,259 and 5,714,225.

The sealing member may be in the form of a paste or in the form of a mouldable ring comprising a hypoallergenic, substantially non-memory putty-like adhesive. In one embodiment of the invention, the sealing member is in the form of a mouldable ring having a slot for facilitating adaptation to stomas having a small diameter and a flange member of any suitable material which is compatible with the adhesives and may be provided with folding or corrugated zones.

The attachment means for attaching an ostomy collection bag may be a system known per se comprising matching coupling rings or matching flanges and adhesive surfaces.

A release liner may for instance be siliconized paper. It does not need to have the same contour as the dressing, e.g. a number of dressings may be attached to a larger sheet of protective cover. The protective cover is not present during the use of the dressing of the invention and is therefore not an essential part of the invention.

An adhesive for attaching the flange of the sealing member to the body side member may be any convenient adhesive being compatible with the materials and surfaces with which the adhesive is in contact.

DESCRIPTION OF THE PREFERRED EMBODIMENTS

Reference is made to FIG. 1 showing an embodiment of an ostomy appliance according to the invention seen from the distal side, said embodiment comprising, taken in direction from the proximal side, a protective sheet or release liner (not shown) covering the adhesive surface to engage with the skin around a stoma, a carrier sheet 1 having protrusions along the periphery thereof and a foam flange 2 for attachment of a receiving bag, and a separate sealing member having a flange 3 for attachment to the body side member, said flange having corrugations 4, and an adhesive sealing body 5. The corrugation is only shown as a simple circular corrugation. Centrally is shown the stoma 6 and furthermore is also shown laterally projecting and diametrically disposed belt-attachment ears 7 projecting outwardly from opposite edges of the ring-shaped body.

Figure 2:
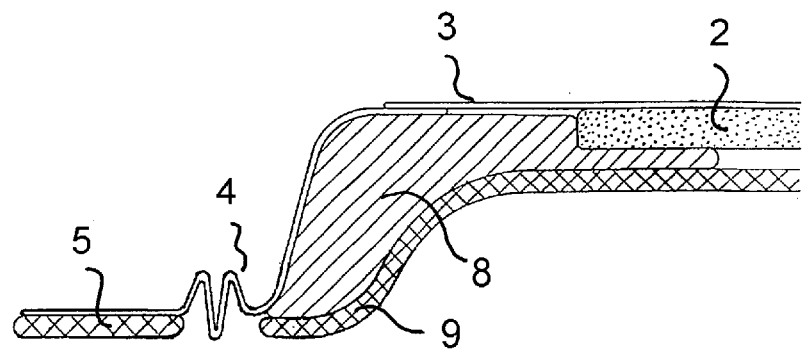
FIG. 2 shows a partial sectional view of a part of an ostomy appliance according to the invention having convex conformation.
Figure 3:
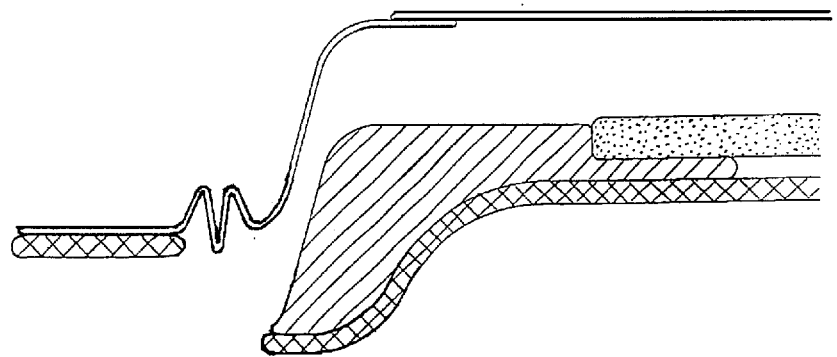
FIG. 3 shows the embodiment of FIG. 2 in which the sealing member is elevated from the body side member and FIG. 4 shows an embodiment of a sealing member according to the invention.

FIGS. 2 and 3 show in a larger scale a partial sectional view of a part of an ostomy appliance having convex conformation with a separate sealing member according to the present invention. This embodiment has a foam flange 2 for attachment of a receiving bag. The separate sealing member has a flange 3 for attachment to the body side member, the flange having corrugations 4, and an adhesive sealing body 5. Furthermore is shown a convex body 8 and an adhesive layer 9 for adhering the body side member to the ostomate's skin.

Figure 4:
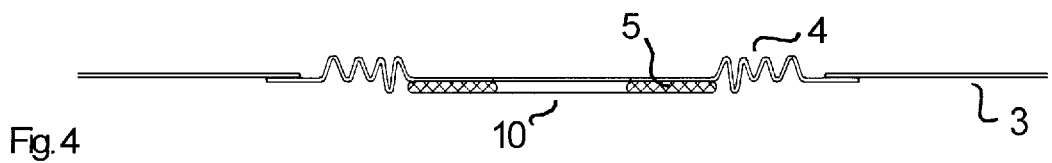

FIG. 4 shows an embodiment of a sealing member according to the present invention having a flange 3 for attachment of the separate sealing member to the body side member, the flange having corrugations 4. The sealing member also has an adhesive sealing body 5, with this embodiment showing the hole 10 for accommodating the stoma.

What is claimed is:

1. An ostomy appliance comprising a body side member including a ring-shaped body having an adhesive wafer with a hole therein for accommodating a stoma and a separate sealing member which, when in use, is placed in said hole to provide sealing against the stoma, said separate sealing member also having a hole for accommodating the stoma and including a mouldable mass of a hypo-allergenic adhesive in the form of a disc that has an outer diameter smaller than a diameter of the hole of the wafer of the body side member, and a flange member extending from an outer rim of said disc, said flange member having outer dimensions greater than the diameter of the hole of the wafer of the body side member for coupling to the body side member, said flange member including a folding zone having a corrugation that allows eccentric displacement of said disc as compared to said flange member.

2. An ostomy sealing member comprising a mouldable mass of a hypo-allergenic adhesive in the form of a disc having a hole for accommodating a stoma and a flange member extending from an outer rim of said disc, said flange member including a folding zone having a corrugation that allows eccentric displacement of said disc as compared to said flange member.

3. A method for placing an ostomy appliance on the abdomen of an ostomate around a stoma or fistula for collecting bodily material emerging therefrom, said ostomy appliance including a body side member having a ring-shaped body with an adhesive wafer with a hole therein for accommodating a stoma and a separate sealing member which, when in use, is placed in said hole to provide sealing against the stoma, said separate sealing member also having a hole for accommodating the stoma and including a mouldable mass of a hypo-allergenic adhesive in the form of a disc that has an outer diameter smaller than a diameter of the hole of the wafer of the body side member, and a flange member extending from an outer rim of said disc, said flange member having a folding zone and outer dimensions greater than the diameter of the hole of the wafer of the body side member for coupling to the body side member, said method comprising the steps of: placing the body side member in a manner in which the stoma is essentially centrally located in the hole of the wafer and in which the adhesive wafer is ensured optimum grip; and shifting the separate sealing member in such a manner that the hole therein is aligned with the stoma and the sealing member is brought into contact with the skin and moulded so as to obtain a sealing contact with the stoma.

4. The ostomy appliance as set forth in claim 1, wherein said mouldable mass is a substantially non-memory putty-like adhesive.

5. The ostomy sealing member as set forth in claim 2, wherein said mouldable mass is a substantially non-memory putty-like adhesive.

* * * * *